United States Patent [19]

Casper et al.

[11] 4,188,196

[45] Feb. 12, 1980

[54] ABSORBER WITH SUCTION PUMP

[75] Inventors: Rudolf Casper; Roland Gröber, both of Leverkusen; Karl-Heinz Schabel, Burscheid; Klaus Siemer, Leverkusen, all of Fed. Rep. of Germany

[73] Assignee: Bayer Aktiengesellschaft, Leverkusen, Fed. Rep. of Germany

[21] Appl. No.: 862,088

[22] Filed: Dec. 19, 1977

[30] Foreign Application Priority Data

Dec. 24, 1976 [DE] Fed. Rep. of Germany ....... 2658739

[51] Int. Cl.² .............................................. B01D 53/04
[52] U.S. Cl. .......................................... 55/270; 55/387
[58] Field of Search ........................ 55/270, 387, 389; 235/92 FL, 92 MT; 364/550, 551, 554

[56] References Cited

U.S. PATENT DOCUMENTS

| 3,171,952 | 3/1965 | Brown ............................ 235/92 MT |
| 3,606,998 | 9/1971 | LaPorte et al. ................... 55/387 X |
| 3,729,996 | 5/1973 | Metz ............................. 235/92 FL X |
| 3,804,942 | 4/1974 | Kato et al. ......................... 55/387 X |
| 3,950,155 | 4/1976 | Komiyama ........................ 55/387 X |
| 4,067,705 | 1/1978 | Kurz ................................ 55/270 X |

*Primary Examiner*—Robert H. Spitzer
*Attorney, Agent, or Firm*—Sprung, Felfe, Horn, Lynch & Kramer

[57] ABSTRACT

In order to control noxious substances in the air, the air to be monitored is continuously drawn through an absorber. An absorber with a suction pump connected downstream is used for this purpose. A particularly small and compact device composed of an absorber and suction pump may be obtained by forming the inlet valve and outlet valve of the suction pump as O-ring disc valves and by providing the pump drive with a light barrier.

3 Claims, 1 Drawing Figure

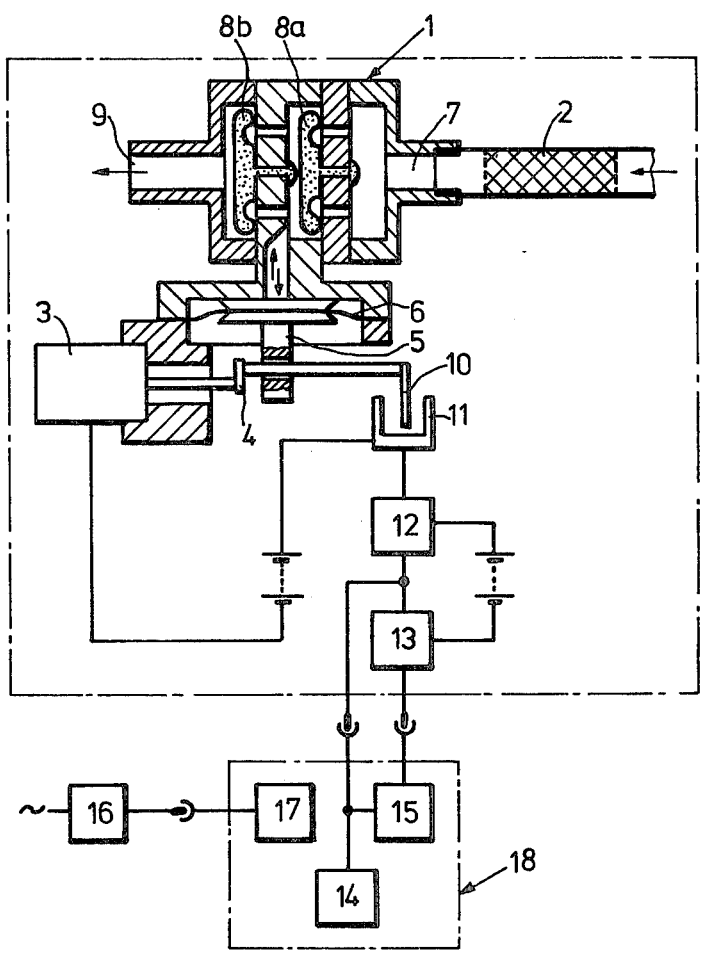

ABSORBER WITH SUCTION PUMP

The invention relates to a device comprising an absorber with a suction pump downstream thereof, for monitoring atmospheric pollution in industrial plants. Such devices are used for example for the protection of personnel. For this purpose, the air is drawn through a small glass tube containing an absorber, for example activated carbon, by means of a suction pump. The contaminants in the air are, absorbed in the activated carbon and may then be analysed, for example according to the end of the layer with the aid of gas chromatographs. If it is assumed that the volume delivered per pump stroke is constant, then the number of pump strokes is a measure of the total quantity of air drawn through the absorber.

The object of the invention is to provide a measuring device consisting of an absorber and suction pump, which can be sufficiently small to enable the entire device to be worn on the body for a working day without being cumbersome. The device must not, however, be miniaturized at the expense of accuracy of measurement and reproducibility. If that were to occur the whole object of measurement that is to say, for example, the quantitative determination of the air drawn through in a working day, could not be achieved with the required degree of accuracy.

According to the invention there is provided a device for monitoring pollutants, comprising an absorber and a suction pump connected downstream thereof, wherein the suction pump has inlet and outlet valves in the form of O-ring disc valves and a pump drive provided with a flag forming part of a light barrier.

The form of valve used in the invention, gives the pump a compact structure. Simultaneously, the seal when the valves are closed, and thus the accuracy of measurement, are improved. The valves used also have the advantage of a smaller dead volume since there are virtually no cavities in the valve.

The barrier at the pump drive allows the pump strokes to be counted electronically. The circuitry required for this purpose consists of integrated circuits and only requires a very low electric power. It may be easily placed in the same housing as the pump. The entire measuring device may for example, be only 110 mm long, 38 mm deep and 60 mm wide.

The invention is described in more detail below with reference to the accompanying drawing, which shows the pump with the light barrier and the associated block diagramm for counting the pump strokes.

Air is drawn through an absorber 2 by a pump 1 connected downstream thereof. The absorber 2 consists of a small glass tube filled with activated carbon. The pump 1 may be a commercial positive-displacement pump, for example a diaphragm pump, and is driven by an electric motor 3 via an eccentric 4. The eccentric 4 transmits its reciprocating movement to a pump ram 5 which is connected to a positive displacement element which in this case is a a diaphragm 6. The air drawn in is conveyed through a suction channel 7 via O-ring disc valves 8 having an inlet valve 8a and an outlet valve 8b to a delivery member 9.

The O-ring disc valves 8 consist of circular silicon rubber discs with a reinforced edge. The reinforced edge forms a sealing bead. The bead may, for example, have a diameter of 2 mm. The disc is about 2 mm thick and is of substantially constant thickness to the edge. A small flag 10 is fixed to the pump ram 5 and interrupts a ray of light from a light barrier unit 11 during each pump stroke. The small flag 10 may alternatively be placed directly on the axle of the motor 3. The electric pulses produced in the light barrier unit are fed to a trigger 12 which normalizes these pulses. The trigger 12 communicates with a counting chain 13 which is also triggerable externally by a gate. When the pump is running the ray of light from the light barrier is periodically interrupted and the normalized pulses are summed in the counter 13. After the measuring procedure, for example when a working shift has expired, the counter 13 is caused to count completely to its final value by pulses from a clock pulse generator 14 of a separate unit 14, 15. The number of pump strokes during the measured period and thus the volume of air drawn through the absorber 2 is derived from the difference between the final value and the additional pulses counted from generator 14. The value can be read directly on the forward-backward counter 15 after corresponding calibration. Although the trigger 12 and the installed counter 13 are integrated into the monitoring unit, the clock pulse generator 14, the forward-backward counter 15 and an associated voltage supply 16, 17 are preferably placed in an external monitoring unit 18.

What we claim is:

1. A device for monitoring polutants, comprising an absorber, a suction pump connected downstream thereof, wherein the suction pump has inlet and outlet valves comprising O-ring disc valves and a pump drive and means for determining the quantity of air drawn through the pump in a given time period comprising a movable flag operatively connected to the pump drive and a light barrier through which the flag periodically moves during the pumping, wherein the determining means comprises counting means for counting the number of light pulses produced by the flag and light barrier and wherein the device further comprises a housing for the pump, flag, light barrier and counting means, said housing being sufficiently small to enable same to be worn on the body of a person for a complete working day without being cumbersome.

2. The device according to claim 1, wherein the counting means includes an externally triggerable digital counter and a first power supply therefor and monitoring means for reading out the data on the counter after a given monitoring period comprising a pulse generator for externally triggering the counter, to count it up to its highest value and a second counter triggered by the pulse generator and preset to count the difference between the highest value and the additional pulses generated by the pulse generator.

3. The device according to claim 2, wherein the monitoring means is external of the housing and has a power supply independent of that for said counting means.

* * * * *